United States Patent [19]

Sertich

[11] Patent Number: 5,800,550
[45] Date of Patent: Sep. 1, 1998

[54] INTERBODY FUSION CAGE

[76] Inventor: Mario M. Sertich, 32368 Regency Ct., Avon Lake, Ohio 44012

[21] Appl. No.: 928,015

[22] Filed: Sep. 11, 1997

Related U.S. Application Data

[63] Continuation of Ser. No. 615,681, Mar. 13, 1996, abandoned.

[51] Int. Cl.$^6$ ........................................................ A61F 2/44
[52] U.S. Cl. ................................................ 623/17; 606/61
[58] Field of Search ................................... 623/17; 606/61

[56] References Cited

U.S. PATENT DOCUMENTS

| | | |
|---|---|---|
| 4,401,112 | 8/1983 | Rezaian . |
| 4,554,914 | 11/1985 | Kapp et al. ........................... 606/69 X |
| 4,599,086 | 7/1986 | Doty ........................................... 623/17 |
| 4,636,217 | 1/1987 | Ogilvie et al. ..................... 623/17 X |
| 4,743,256 | 5/1988 | Brantigan . |
| 4,834,757 | 5/1989 | Brantigan . |
| 4,878,915 | 11/1989 | Brantigan . |
| 4,892,545 | 1/1990 | Day et al. . |
| 5,062,850 | 11/1991 | MacMillan et al. . |
| 5,071,437 | 12/1991 | Steffee . |
| 5,147,402 | 9/1992 | Bohler . |
| 5,171,278 | 12/1992 | Pisharodi . |
| 5,192,327 | 3/1993 | Brantigan . |
| 5,222,954 | 6/1993 | Baker et al. . |
| 5,236,460 | 8/1993 | Barber . |
| 5,263,953 | 11/1993 | Bagby . |
| 5,314,477 | 5/1994 | Marnay . |
| 5,360,430 | 11/1994 | Lin . |
| 5,397,364 | 3/1995 | Kozak et al. . |
| 5,401,269 | 3/1995 | Buttner-Janz et al. . |
| 5,456,724 | 10/1995 | Yen et al. ................................. 623/16 |
| 5,514,180 | 5/1996 | Heggeness et al. .................. 623/17 |
| 5,522,899 | 6/1996 | Michelson ............................. 623/17 |
| 5,578,035 | 11/1996 | Lin ........................................... 606/68 |
| 5,658,335 | 8/1997 | Allen ....................................... 623/17 |
| 5,702,391 | 12/1997 | Lin ........................................... 606/61 |
| 5,723,013 | 3/1998 | Jeanson et al. ....................... 623/17 |

FOREIGN PATENT DOCUMENTS

| | | | |
|---|---|---|---|
| 176728 | 4/1986 | European Pat. Off. ................ 623/17 |
| 40515548 | 1/1993 | Japan ....................................... 623/17 |
| 1424826 | 9/1988 | U.S.S.R. .................................. 623/17 |
| 1662534 | 7/1991 | U.S.S.R. .................................. 606/61 |
| 95/25486 | 9/1995 | WIPO ...................................... 623/17 |

OTHER PUBLICATIONS

Article entitled "Management of Iatrogenic Spinal Stenosis Complicating Placement of a Fusion Cage" from SPINE vol. 21, No. 20, pp. 2383–2386 ©1996, Lippincott–Raven Publishers.

Paper entitled "Current Experience with the Ray—TFC—The Threaded Fusion Cages..." Presented by C. D. Ray on Apr. 8, 1993 at Japanese Orthopedic Assn.

Paper entitled "Posterior Lumbar Interbody Fusions by Implanted Threaded Titanium Cages" by C. D. Ray circa 1993.

Cover page and p. 19 of Spinetech brochure captioned "Posterior Surgical Technique" BAK Interbody Fusion System.

Cover page and p. 20 of Spinetech brochure captioned "Anterior Surgical Technique" BAK Interbody Fusion System.

*Primary Examiner*—David H. Willse
*Attorney, Agent, or Firm*—Fay, Sharpe, Beall, Fagan, Minnich & McKee

[57] ABSTRACT

A prosthetic device adapted for fusing together adjoining vertebrae connected by tissue of a collapsed disc includes an inert generally rectangularly shaped support body adapted to be seated on hard end plates of vertebrae. The support body has top and bottom faces. A first peg is movably mounted in a first aperture located in the support body. The first aperture terminates at one of the top and bottom faces of the support body. The first peg projects away from the one of the top and bottom faces and into an adjacent first vertebra to secure the support body in place relative to the first vertebra. The support body is preferably hollow so as to allow the ingrowth of osseous tissue.

24 Claims, 5 Drawing Sheets

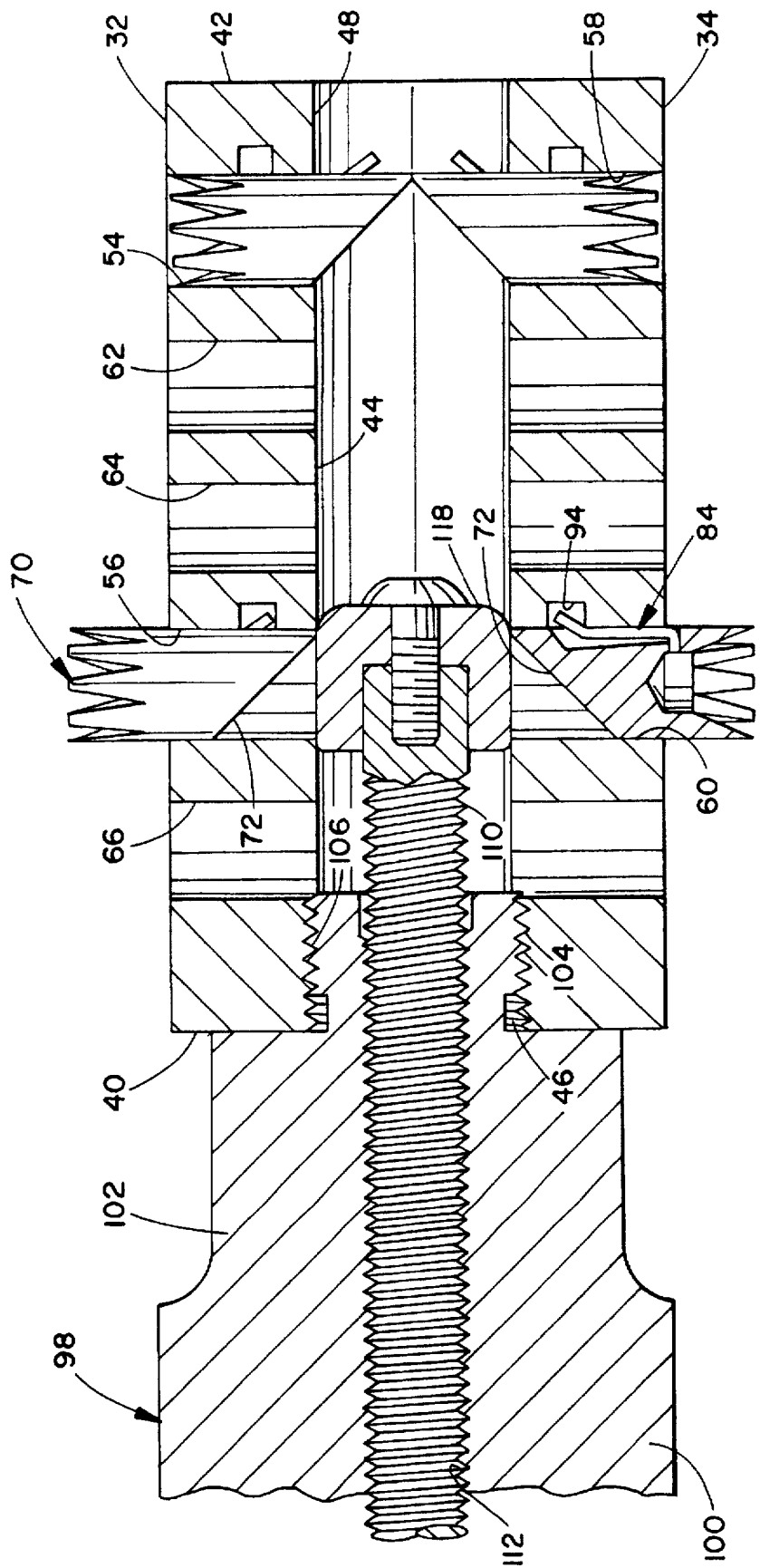
FIG. IA

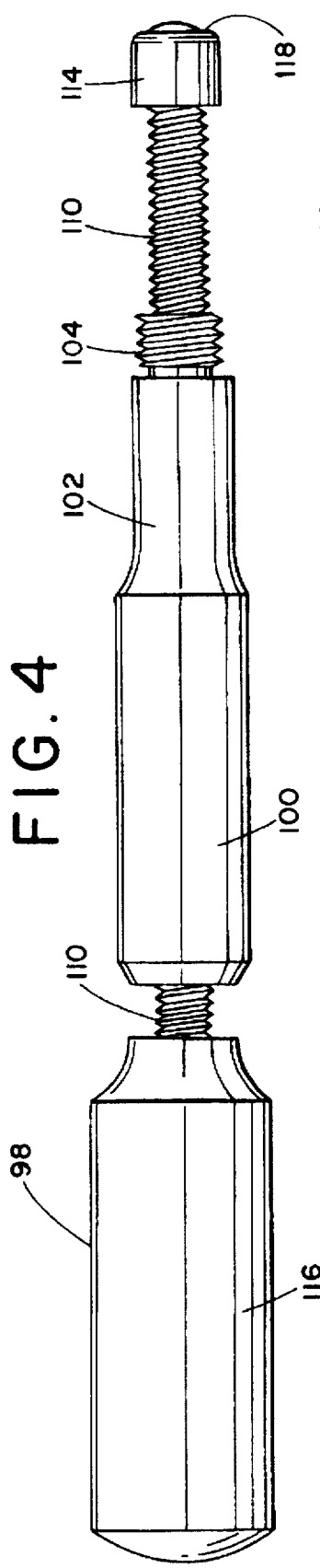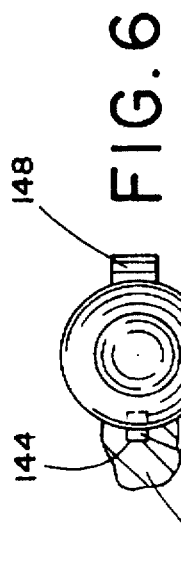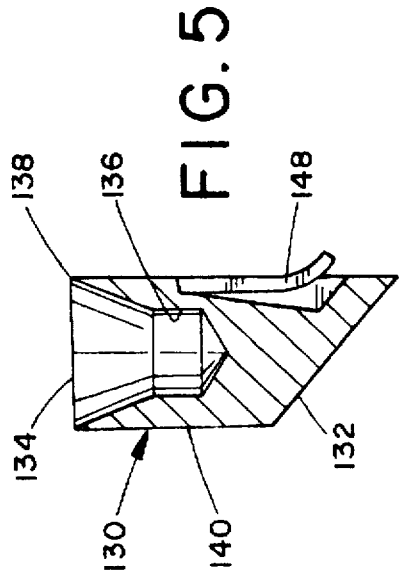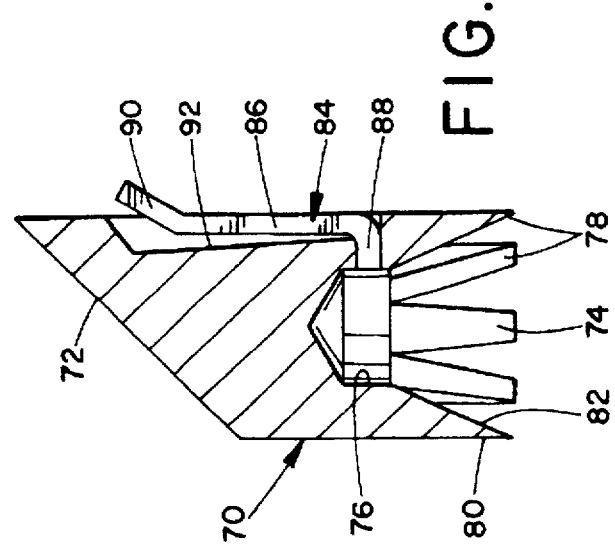

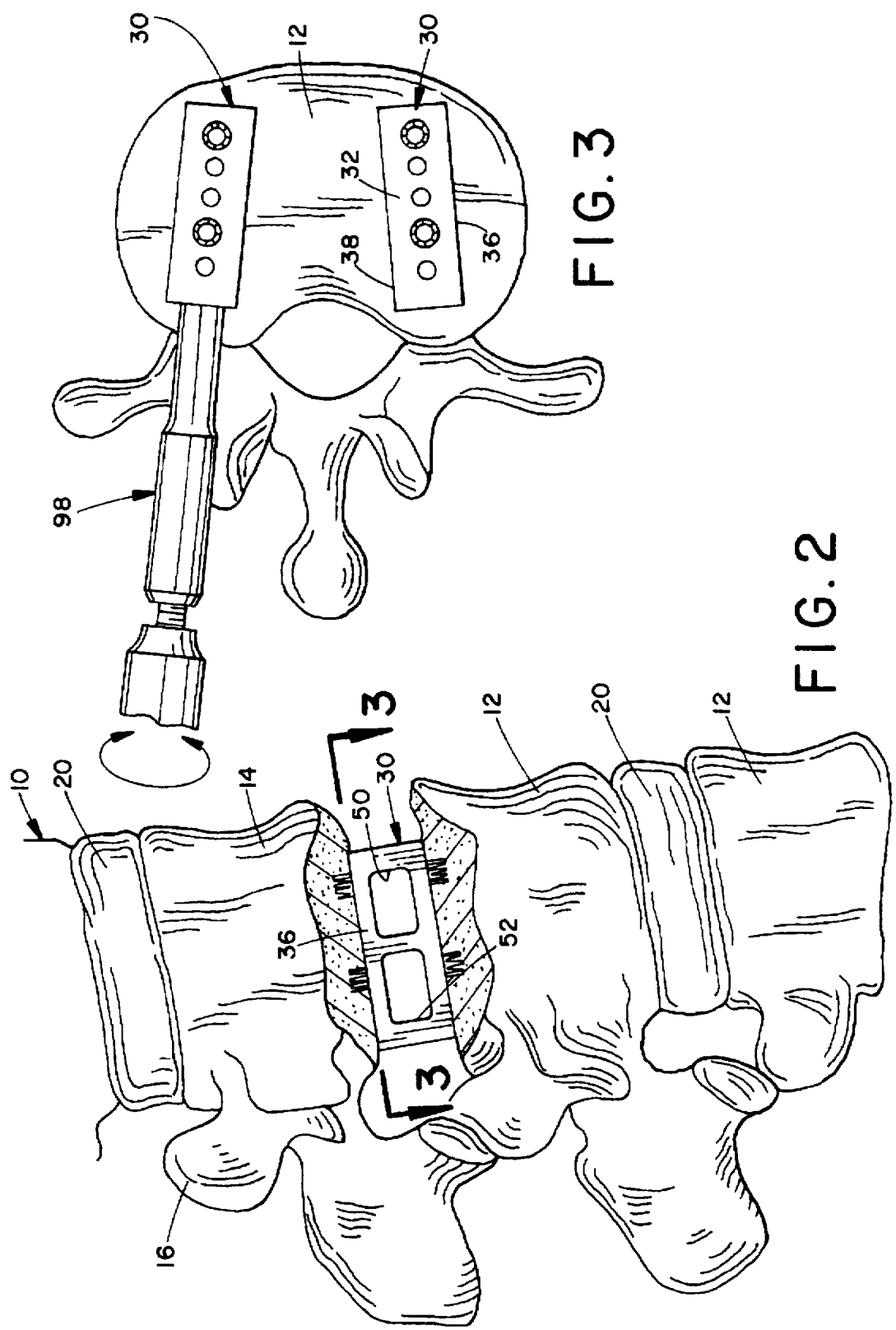

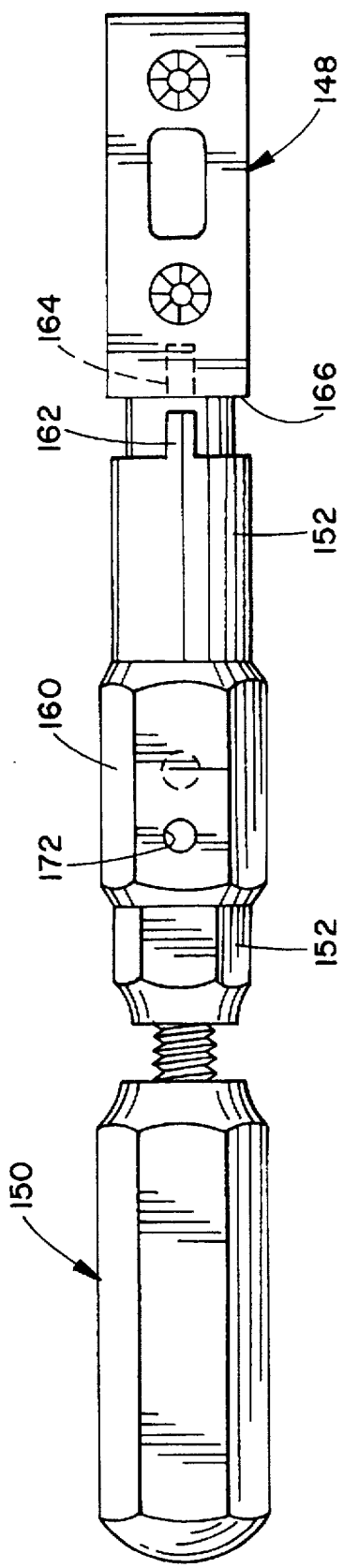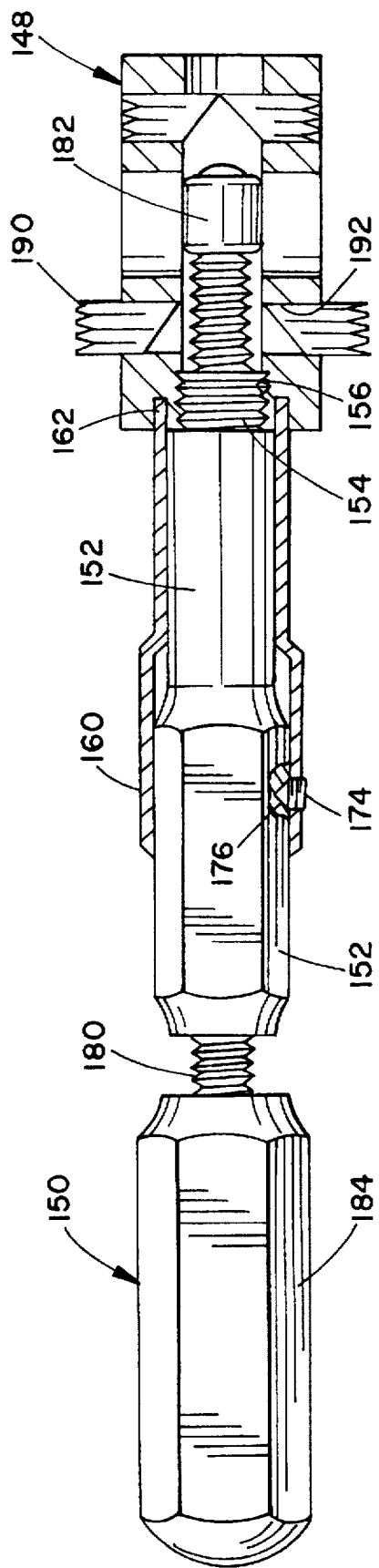
FIG. 7A
FIG. 7B

INTERBODY FUSION CAGE

This application is a continuation of U.S. patent application Ser. No. 08/615,681 Mar. 13, 1996, now abandoned.

BACKGROUND OF THE INVENTION

This invention relates to spinal implants. More specifically, the present invention relates to an implant which is to be placed into the intervertebral space left after the removal of a damaged spinal disc to assist in promoting interbody fusion.

Degeneration of the intervertebral disc is believed to be a common cause of the final pathology of the spine as well as of back pain. The changes in the aging nucleus include decreases in the content of proteoglycans, and the ratio of keratin sulphate to chondroitin sulphate, causing the nucleus to lose water content and swelling pressure. This affects the disc's ability to tolerate load and causes further injury to the fiber attachments of the surrounding annular ring. The damage to the thinner posterior annulus leads to displacement of the disc material.

There are three basic treatments currently used to alleviate lower back pain and the nerve injury caused by injured or degenerated discs. These are, first, conservative care, second, a laminectomy and discectomy and, third, interbody fusion. Most low back problems are self limiting and approximately 75 to 80% of patients recover within six weeks with or without medical treatment. Therefore, conservative care is the most common option. However, cases that go on to have prolonged disability are the primary contributors to the great expense of low back pain.

In the more severe cases, the disc tissue is irreparably damaged thereby necessitating the removal of the entire disc. Laminectomy gives good results in the short-term by removing the herniated disc material (usually the nucleus) which is causing the low back pain or sciatica by compressing the spinal nerve, or by chemical irritation. But, the removal of the nucleus in the laminectomy procedure actually causes the compressive load to be distributed even further on the annular ring, narrowing the disc space further. This promotes reherniation, degenerative changes in the facet joints and a narrowing of the neural foramen. When the disc nucleus is removed without subsequent stabilization, the same disabling back pain often recurs due to persistent inflammation and/or instability.

An interbody fusion maintains disc height, helps protect the nerve root in the neural foramen and restores weight-bearing to anterior structures. It also restores the annulus to tension and immobilizes the unstable, degenerated intervertebral disc. Anterior approaches and fusion in the cervical region have gained wide acceptance by both neurosurgeons and orthopedic surgeons as treatment for a herniated disc, spondylosis and trauma. The experience in the treatment of lower lumbar spine problems has been less encouraging. Posterior approaches to fusion have had variable success, especially with multiple level fusions. Pseudoarthrosis and crushing of the bone grafts seem to represent different problems than those presented in the cervical spine. More recently, pedicle screws and rods have allowed surgeons to reduce degenerative deformities and immobilize the motion segment, but they have not eliminated the need for weight-bearing support of the anterior column. This lack of anterior column support has led to a rash of well-publicized broken screws.

While many types of vertebral prosthetic devices have been proposed, the success ratio for these devices has been very low and the surgical procedures for installing them have been very complicated and traumatic to the patient. It is known to use interbody fusion cages made of biologically acceptable but completely inert material where the cages are bottomed in channels or grooves of adjoining vertebrae and receive bone ingrowth which fuses the structure to the bone and forms a living bone bridge across the fusion area. However, these cage implants have relied significantly on the concomitant use of the pedicle screw system to insure fusion and to guard against retropulsion of the cage. Retropulsion of the cage into the neural canal obviously poses a significant danger. In addition, the need for cage and pedicle screw procedures in combination is additive in terms of the risk of placement of the hardware and the length of surgical time.

Titanium threaded cages have been used more recently, often eliminating the need for pedicle screw instrumentation. Such cages are placed either via anterior surgical exposure or via posterior rods. The anterior approach represents a more formidable problem with risk of injury to vascular structures, viscera and sympathetic structures. The posterior approach requires the use of a cylindrical cage which must overlap the disc space by approximately 3 millimeters in each vertebral body. Therefore, a typical 11 to 13 millimeter disc space is spanned by a 16 to 18 millimeter cage. Retraction of neural elements to this extent, especially at mid-lumbar levels and in the presence of postoperative scarring, in the case of recurrences, is quite difficult and predisposes to nerve root injury.

Accordingly, it has been considered desirable to develop a new and improved interbody fusion cage which would overcome the foregoing difficulties and others while providing better and more advantageous overall results.

SUMMARY OF THE INVENTION

The device comprises an inert rectangularly shaped support body for seating on hard end plates of vertebrae, the support body having solid top and bottom faces. The shape is narrower in width than in height. This design allows placement in the disc space along the narrow side, then rotation of the device 90° to simultaneously lock the device in position, and distract the collapsed disc space. To avoid further dislodgement, anchoring pegs are movably mounted in the top and bottom faces of the support bodies. The pegs preferably comprise a body having a solid proximal end and an apertured distal end. The proximal end is tapered to allow extension of the pegs into the adjacent vertebrae by the movement of a piston of the insertion tool.

If desired, the pegs can further comprise a means for preventing a rotation of the peg in the support body. The means can comprise a key extending away from the outer periphery of the peg. The key cooperates with a key way defined in the support body. Preferably, the device further comprises a means for locking the first peg in place in relation to the support body when the first peg has been projected outwardly of the support body. Preferably the support body comprises a hollow three dimensional member, including six interconnected walls defined by an interior cavity and at least one opening in each wall of the member to allow for ingrowth of osseous tissue into the interior cavity of the body.

In accordance with another aspect of the invention, a method is provided for fusing together adjacent vertebrae having spaced opposed faces with a disc space therebetween.

More particularly in accordance with this aspect of the invention, the method comprises the steps of providing a first rigid rectangular support body, which is higher than it is wide, and has a first peg mounted for movement therein. The first support body is inserted in an excised disc space between adjacent vertebrae in a sidewards manner and is then rotated 90° so that the support body spans the disc space to provide a first strut maintaining the disc space. The first peg is then projected from the support body into the first vertebra. The first peg can be then locked in the support body to prevent movement therebetween.

Preferably a second peg is extended from the support body into a second vertebra and the second peg is locked in the support body to prevent movement therebetween. The method preferably further comprises the step of inserting a second rectangular support body in an excised disc space between adjacent vertebrae in a sideward manner and then rotating the second support body 90° to provide a second strut, spaced from the first strut. The heights of the first and second support bodies are correlated in order to maintain the disc space. The method preferably further comprises the step of reducing the possibility of nerve injury by forming the first support body so that it is a parallelepiped and is narrower in width than it is tall. Finally, the method preferably further comprises the step of facilitating bone ingrowth around the walls of the first support body in bonded relation to the vertebrae.

An advantage of the present invention is a provision of a new and improved interbody fusion cage. The cage is improved due to its shape, it is improved due to an internal locking mechanism and it is improved due to the attachment of insertion tools to the cage which serve to position, rotate and lock the cage in the desired position.

Another advantage of the present invention is a fusion cage which is rectangular in shape so that it is narrower in width than in height. This design does not require excessive removal of the articulating surfaces of adjacent vertebrae nor any removal of midline elements. It also does not require excessive retraction of the neural elements thereby reducing the possibility of nerve injury.

Yet another advantage of the present invention is the provision of an interbody fusion cage which can be inserted through a typical disc laminectomy section portal.

A most important advantage of the rectangular shape of the fusion cage, that is narrower in width than in height, is the ease of insertion of the cage into the collapsed disc along the narrower side. Rotating the cage by 90° can restore or maintain the normal geometry of the intradiscal space, such as disc height and sagittal angle.

A further advantage of the present invention is the provision of an interbody fusion cage which is self-stabilizing to avoid dislodgement after implantation. Stabilization is accomplished by anchoring pegs movably mounted in the cage. With this design, there is no need for pedicle screw stabilization, thus simplifying the amount of surgery needed and reducing the amount of hardware implanted in a patient's spine.

A still further advantage of the present invention is the provision of an interbody fusion cage with anchoring pegs which have inner and outer surfaces that both frictionally engage the bone of the adjacent vertebrae in order to solidly anchor the pegs in place and prevent the pegs' easy removal from the vertebrae.

Yet another advantage of the present invention is the provision of an anchoring peg for an interbody fusion cage wherein the peg has serrated edges which do not offer as much resistance to penetration of the bone of the adjacent vertebrae as do conventional pins, and yet improve the grip and retention of the peg in the adjacent vertebrae to retard its dislodgement therefrom.

An additional advantage of the present invention is the provision of insertion tools which serve many functions for the interbody fusion cage. The insertion tool serves as a stabilizing handle for the cage during the process of introducing the cage into the disc space.

A further advantage of the present invention is the attachment to an interbody fusion cage of an insertion tool which serves as a torque wrench which rotates the cage and distracts the disc space simultaneously locking the cage and expanding the collapsing disc space.

A yet further advantage of the present invention is the provision of an insertion tool for an interbody fusion cage wherein the tool has a movable piston which serves to extend the pegs of the cage into the adjacent vertebrae.

Yet an additional advantage of the present invention is the provision of an insertion tool which can be removed providing an interbody fusion cage which has hollow areas that can be packed with autologous cancellous bone or other material to promote bone ingrowth and fusion.

Still other benefits and advantages of the invention will become apparent to those of average skill in the art upon a reading and understanding of the following detailed specification.

BRIEF DESCRIPTION OF THE DRAWINGS

The invention may take physical form in certain parts and arrangements of parts, preferred embodiments of which will be described in detail in this specification and illustrated in the accompanying drawings which form a part hereof and wherein:

FIG. 1A is a side elevational view in cross-section of an interbody fusion cage or support body according to a first preferred embodiment of the present invention together with an inserting tool therefor;

FIG. 1B is an enlarged side elevational view in cross section of an anchoring peg of the interbody fusion cage of FIG. 1A;

FIG. 2 is a side elevational view of a portion of a vertebral column showing an excised disc space between adjacent vertebrae and the interbody fusion cage of FIG. 1A secured therebetween;

FIG. 3 is a top plan view of FIG. 2 along line 3—3;

FIG. 4 is a side-elevational view in cross-section of the inserting tool for the interbody fusion cage of FIG. 1A;

FIG. 5 is a cross-sectional view of a retaining peg for an interbody fusion cage according to a second preferred embodiment of the present invention;

FIG. 6 is a top plan view, partially in cross-section, of the retaining peg of FIG. 4 with a portion of a fusion cage according to the second preferred embodiment of the present invention.

FIG. 7A is a top plan view of an interbody fusion cage and an inserting tool therefor according to a third preferred embodiment of the present invention with a sleeve of the tool being shown in a retracted position;

FIG. 7B is a side elevational view of the cage and tool of FIG. 7A partially in cross-section with the sleeve of the tool being shown in an extended position;

DETAILED DESCRIPTION OF THE PREFERRED EMBODIMENTS

Figure 9:
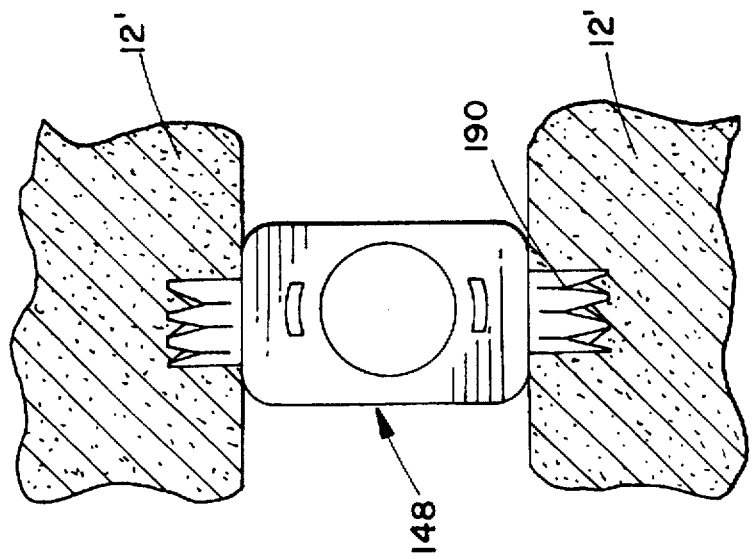

Referring now to the drawings wherein the showings are for purposes of illustrating preferred embodiments of the invention only and not for purposes of limiting same, FIG. 2 illustrates an interbody fusion cage, according to the present invention, inserted in a spine 10 replacing a damaged or diseased disc between a pair of adjacent vertebrae 12.

The human spine 10 is a flexible structure comprised of thirty-three (33) vertebrae 12. The vertebrae each have an anterior side 14 and a posterior side 16. The vertebrae are separated from each other and cushioned by fiber cartilage in structures called intervertebral discs 20. If the spine is injured or becomes diseased, these discs are often surgically removed. Such disc injuries can happen in the neck, in the thoracic region and in the lumbar region. The more frequent injuries are in the lower lumbar region.

It is known that the vertebral body has regions of differing bone strength. It has been discovered that a central kidney-shaped region of the vertebral body comprises mostly weak cancellous bone. An annular kidney-shaped region around the central portion contains stronger bone while the ring apophysis has the strongest bone of the vertebral body. With this in mind, the present invention strives to load those regions of the vertebral body that have the stronger load bearing capability.

When a disc 20 is excised from between a pair of adjacent vertebrae 12, two spaced support bodies 30, according to the present invention, are inserted between the vertebrae. The support bodies, or interbody fusion cages, 30 function as struts and are used to maintain intravertebral disc spacing, as illustrated in FIG. 2. The two bodies 30 are identical. Therefore, only one of the bodies will be discussed, it being appreciated that the other body has the identical components.

With reference now also to FIG. 1A, the support body 30 comprises a top wall 32, a bottom wall 34, a first side wall 36 (FIG. 3), a second side wall 38 (FIG. 3) and first and second end walls 40 and 42. Thus the implant body is rectangular in shape and, as can be seen from a comparison of FIGS. 2 and 3, the body 30 is taller than it is wide. The body 30 can typically measure between 9×11 millimeters and 11×13 millimeters, which is the height of the typical human disc.

A central passageway 44 extends longitudinally in the body 30 from a first end wall opening 46 to a second end wall opening 48. As illustrated in FIG. 2, a first horizontal passage 50 and a second horizontal passage 52 extend through the body 30 from the first to the second side walls 36 and 38 of the body. These passages 50 and 52 communicate with the central passageway 44. Located in the top wall 32 are first and second peg openings or guide holes 54 and 56. Located in the bottom wall are third and fourth peg openings or guide holes 58 and 60. The first and third peg openings 54 and 58 are aligned as are the second and fourth peg openings 56 and 60, as is evident in FIG. 1. Preferably, three spaced vertical passages 62, 64 and 66 extend through the body from the top wall 32 to the bottom wall 34. Each of these passages also communicates with the central passageway 44.

The support body 30 can be made of an inert metal substrate, such as stainless steel, cobalt, chromium, molybdenum alloys, titanium or the like, or compounds thereof, and can have a porous coating of metal particles of a similar substrate metal. Alternatively, the implants can be made of radio-lucent material, such as carbon fiber reinforced polymers known commercially as "PEEK" (polyether etherketone) or ULTRAPEK (polyether ketone, ether ketone, ketone). Also, polycarbonate, polypropylene, polyethylene and polysulphone plastics which are reinforced with glass fibers or carbon fibers can be used. Such materials are available from ICI Industries of Wilmington, Del.; Fiber-Rite Corporation of Winona, Minn. or BASF Corporation.

Preferably, movably mounted in each of the peg openings 54, 56, 58 and 60 is a respective anchoring peg 70. With reference now to FIG. 1B, each of these pegs includes a tapered proximal end 72 and a toothed distal end 74. Located in the peg distal end 74 is preferably conical central valley or cavity 76 terminating in a plurality of spaced teeth 78. Preferably, eight such teeth are provided, although any other suitable number of teeth can be used. The spaced teeth and conical valley permit a strong anchoring of the peg 70, and hence the body or cage 30, in the cortical bone. More specifically, the anchoring pegs 70 provide a serrated edge which offers less resistance to penetration into the vertebral bone than a solid edge would. In addition, the pegs provide a significantly improved grip, in relation to a conventional pin, to retain the pegs in place in the bone. The better grip is provided because both an outer surface 80 and an inner surface 82 of each tooth 78 frictionally engages the bone to hold the peg in position in the bone once the peg distal end is inserted in the bone.

Preferably the pegs are made of a suitable conventional metal such as the metals mentioned previously with regard to the body 30. The pegs 70 can, if desired, be right cylindrical in shape. On the other hand, the pegs could have any other suitable desired cross-section, or even a variable cross-section, along the length of the peg if the peg openings in the body 30 are also suitably configured. While two sets of pegs are illustrated in the body 30, it should be appreciated that any desirable number of pegs can be located in the body.

Two spaced pegs along each of the top and bottom surfaces 32 and 34 are considered advantageous from the standpoint that the body 30 can then not rotate in relation to the adjacent vertebrae 12 once the pegs 70 are protruding into the cortical bone. The pegs also prevent the body from sliding longitudinally or laterally in relation to the vertebrae 12.

Preferably, a securing means 84 is provided for retaining the pegs 70 in an extended position in relation to the body 30. The securing means can comprise, if desired, a flat locking spring 86 which is fastened at one end 88 to the peg 70 and has a free end 90 extending away from the peg. The spring is housed in a recess 92 of the peg. The free end 90 of the spring 86 can snap into a slot 94 formed in the body 30 when the peg 70 is in its extended position. This action locks the peg in relation to the body and prevents a retraction of the peg into the body. Preferably the locking spring 86 is made from a suitable conventional metal.

While FIG. 3 illustrates a design in which the securing means 84 comprises a peg locking spring 86 and a slot 94 in the support body 30, it should be appreciated that other ways could be provided for securing the peg in place in the body. One such way may be to simply provide a tight fit of the peg in the body to retard by friction any unwanted sliding movement of the peg in relation to the body.

With reference now also to FIG. 4, a tool 98 is employed for inserting the body 30 and securing it in place between a pair of adjacent vertebrae 12. The tool can comprise a first handle section 100 having a forward tip 102 with an annular outer threaded section 104. The threaded section on the first handle section tip cooperates with a threaded bore 106 provided in the implant body first end wall opening 46.

Movably mounted in the first handle section 100 of the tool 98 is a threaded rod 110. The rod 110 is accommodated in a suitably threaded bore 112 (FIG. 1A) extending longitudinally through the first handle section 100 of the tool 98. Located on a first end of the rod 110 is a piston 114. The second end of the rod 110 is secured to a second handle section 116. The two handle sections 100 and 116 are longitudinally movable in relation to each other as the rod 110 is advanced and retracted in the threaded bore 112 extending through the first handle section 100.

With reference now again to FIG. 1A, the piston 114 includes a piston face 118 which contacts the tapered proximal end 72 of each peg 70, and as the rod 110, which can also be considered to be a piston stem, is advanced, pushes the pegs outwardly in relation to the body 30 until the free end 86 of each peg locking spring 82 snaps into its respective slot 90 in the body. Then the piston 114 can be advanced in the central passageway 44 by rotating the threaded rod 110 until the piston face 118 contacts the second pair of opposing pegs 70. These pegs are extended in the same way as the first pair of pegs.

Then the piston 114 can be retracted. The tool 98 can be removed from the body 30 by unthreading the threaded section 104 of the first handle section 100 from the bore 106 in the body. At that point, the central passageway 44 can be packed with autologous cancellous bone, or even with other material. If desired, a small conventional cap (not illustrated) can then be placed over the exposed intracanal opening, the opening 46 in the body 30, is seal this opening.

The body 30 is inserted into the prepared disc space with the tool 98. As mentioned, the tool 98 serves both as a handle to hold the implant—as it is inserted in the desired location—and as a propelling mechanism to extend the pegs into the adjacent end plate and cortical bone to stabilize the body in place. Thus, the tool 98 serves as an internal miniaturized expansion mechanism for the pegs 70. With this design, no external expansion mechanism need be used. Due to the limited amount of space which is available between a pair of adjacent human vertebrae, such an external mechanism would be difficult to employ. Moreover, the tool and the pegs serve as a self-tapping anchoring means since pre-drilling of holes in the cortical bone is well nigh impossible due to the limited amount of space which is available between adjacent vertebrae.

With reference now to FIG. 5, a different type of retaining peg 130 is there illustrated. This peg has a tapered proximal surface 132 and a planar distal surface 134. The peg includes a preferably conical central valley or cavity 136 defined by an annular cutting lip 138. The annular cutting lip and the conical valley permit a strong anchoring of the peg 130 in the cortical bone. As shown in FIG. 6, the peg can have a substantially right cylindrical exterior periphery 140. If desired, a key 142 can be fastened to the exterior periphery of the peg. The key 142 cooperates with a suitable keyway 144 defined in a support body 146 to serve as a means for preventing a rotation of the peg in the body. The key 142 is not illustrated in FIG. 5 for the sake of simplicity. Both FIGS. 5 and 6 illustrate a locking means 148 which is similar to the locking means discussed with regard to FIGS. 1A and 1B.

While a key and keyway are here illustrated as the means for preventing rotation of the peg in the body, it should be appreciated that other conventional ways of preventing a rotation of the peg in the implant body can also be employed. For example, one means of preventing rotation of the peg in the body would be to provide pegs which are not cylindrical in cross-section. One suitable non-cylindrical cross-sectional shape which could be used is an oval shape. Alternatively, one could conceivably use a cruciform cross-section shaped peg.

An important design consideration for the pegs 70 and 130 illustrated in FIGS. 1A, 1B and 5 is that the proximal ends of the pegs, i.e., the ends which are propelled outwardly by sliding contact with the piston face 118 need to be solid in order to ensure that the piston face smoothly slides against the peg proximal end as the piston 114 is rotated forward in the threaded bore 112 of the inserting tool first handle section 100. Thus, the pegs have a solid lower section and a hollow upper section which may be provided with teeth or serrations if desired.

A method for fusing together adjoining vertebrae with the interbody fusion cages, or support bodies, according to the present invention will now be described. When a diseased or degenerated disc is encountered in the spine, whether the spine is human or otherwise, a laminectomy is performed to remove the herniated disc material. Then, transverse opposed first channels are cut in the spaced opposed faces of the vertebrae on one side of the neural canal. Preferably the channels are cut from the posterior side of the vertebrae such that the opposed first channels are not cut all the way through to the anterior side of the vertebrae. Then a first support body 30 is inserted through the open ends of the opposed first channels. The support body is so sized as to span the disc space and prevent the adjoining vertebrae from approaching each other. The body 30 is inserted by means of the tool 98. To this end, the body 30 can be threaded onto the threaded tip 104 of the first handle section 100 of the tool 98.

Once the body is correctly positioned between the vertebrae, the several pegs 70 therein are extended into the opposing surfaces of the two vertebrae. To this end, the piston 114 of the tool 98 is advanced so as to urge the opposing tapered surfaces 72 of the first set of pegs 70 away from each other and into the opposed vertebrae. Once these pegs have been advanced to their full extent, they are locked in position via the securing means 80. Then the piston 114 can be further advanced down the bore 44 until it encounters the opposed tapering surfaces 72 of the second pair of pegs 70. As the piston is advanced forward in the tool 98 via the threaded stem 110, it will cause the second pair of pegs 70 to also extend into the opposed vertebrae and eventually be locked in position. Thereafter, the piston 114 can be retracted via its threaded stem 110 by reversing the direction of rotation thereof.

Then the first handle section 100 can be unthreaded from the bore 106 on the implant body first end wall opening 46 and removed. Subsequently, the central passageway 44 can be packed with autologous cancellous bone or other material to promote bone ingrowth and fusion. A cap (not illustrated) can then be placed over the opening 46 to prevent the packed insert material from falling out of the central passageway 44. The presence of cancellous bone or other material in the central passageway 44 also acts as a means for preventing the pegs 70 from sliding back into the cage 30. The bone or other material which is packed into the central passageway 44 will likely also enter the several passages 62, 64 and 66 thereby approaching the opposed vertebrae to begin the fusion process more quickly.

The same process then takes place on the other side of the neural foramen in order to implant the other cage 30. It should be appreciated that the insertion of the two cages must be achieved within a relatively small surgical "window" on both sides of the neural foramen through which the spinal cord passes. The diameter of the space available for access limits the size of the cage which can be placed between adjacent vertebrae to spread them and immobilize the joint while bone growth occurs. It is, therefore, an advantage to have cages which are narrower than they are tall, as disclosed in the instant invention. It should also be appreciated that two smaller implants, as long as they are well seated, will offer better stability than one of the same size.

The process of drilling and implanting the second body 30 will not loosen the first body 30 since the locking pegs 70 insure that the body is well secured to the adjacent vertebral faces. Thus the problem of a loosening of the bodies is overcome by using bodies which have anchoring pegs that can protrude therefrom to secure the bodies in place.

Figure 8:
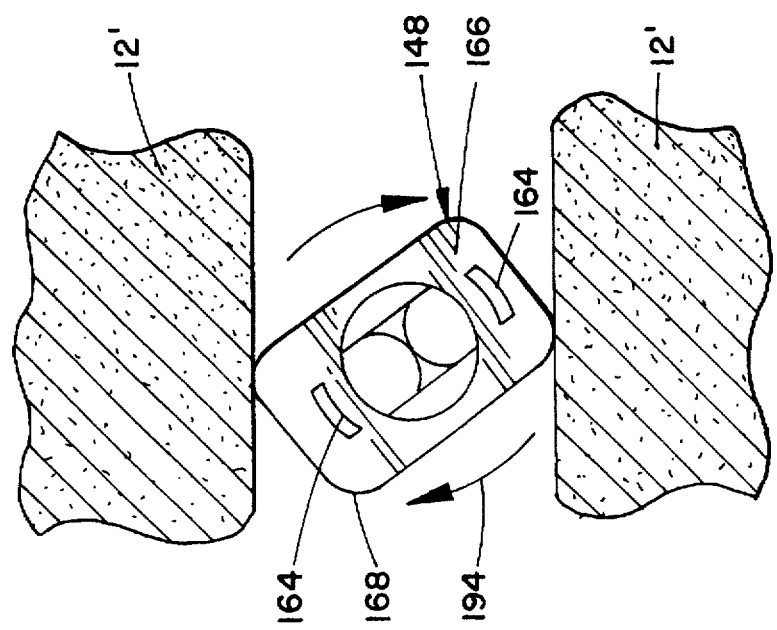
FIG. 8 is an end elevational view of the cage of FIG. 7A in the process of insertion between a pair of adjacent vertebrae; and, FIG. 9 is an end elevational view of the cage of FIG. 8 after it has been inserted between the vertebrae and with the retaining pegs thereof being located in an extended position.

With reference now to FIGS. 7–9, a third preferred embodiment of a fusion cage and an insertion tool therefor are there illustrated. In this embodiment, like components are identified by like numerals with a primed suffix (') and new components are identified by new numerals.

FIG. 7A shows an implant body 148 which is held by a tool 150. The tool has a first handle section 152 which has a threaded front end 154 by which it can be selectively secured to the implant body, via suitable mating threading 156 in the channel of the implant body. Slidably mounted on the first handle section 152 is a sleeve 160. The sleeve includes a pair of projecting fingers 162 (see FIG. 7B). The fingers are located 180° from each other around the front end of the sleeve as is evident from FIGS. 7A and 7B. The fingers each cooperate with a respective slot 164 formed in a first end 166 of the implant body 148.

With reference now also to FIG. 8, it is evident that the implant body has four radiused corners 168. These corners enable the implant body to be easily rotated.

With reference now again to FIG. 7A, an aperture 172 extends through the sleeve 160. Mounted via suitable means in the aperture 172 is a fastener 174 as illustrated in FIG. 7B. When the fastener is in its projecting position, it contacts an indentation 176 formed in the outer surface of the first handle section 152 in order to secure the sleeve in a projecting condition (as shown in FIG. 7B) in relation to the first handle section 152.

Extending through a longitudinal threaded bore in the first handle section 152 is a threaded rod 180. The rod has on a first end a piston 182 and on its second end a second handle section 184. The piston 182 is employed to urge anchoring pegs 190, mounted in apertures 192, outwardly of the implant body 148.

It is evident from FIGS. 7A and 7B that the implant body 148 is rectangular such that it is taller than it is wide. With reference now to FIG. 8, the implant body 148 is inserted sidewards between a pair of adjacent vertebrae 12'. Once the sleeve 160 is locked in its forward position such that the fingers 162 thereof are engaged in the slots 164, as is evident from FIG. 7B, the first handle section 152 can then be rotated in relation to the second handle section 184 by grasping the sleeve 160 with one hand and the second handle section 184 with the other hand and exerting a rotational force on the sleeve as well as on the implant body 148. The implant body is thus rotated by 90° as is illustrated by the arrows 194 in FIG. 8. This rotation of the implant body 148 distracts the disc space and simultaneously locks the body 148 in place. Because of the radiused corners 168 of the body 148, such rotation of the body will not cause a scraping of the facing surfaces of the vertebrae.

Once the body has been rotated 90° as is illustrated in FIG. 9, the second handle section 184 can be rotated so as to advance the piston 182 and extend the anchoring pegs 190 in much the same manner as discussed previously with regard to the embodiment of FIGS. 1–4. The sleeve 160 is retracted away from the implant body 148 by loosening the fastener 174 and allowing the sleeve to move backwards in relation to the first handle section 152. Then the tool 150 can be removed from the body 148 by unthreading the first handle threaded section 154 from the threaded area of the body 148.

The reason for the sleeve 160 is to prevent an overtorquing of the first handle section threaded area 154 in relation to the threaded section 156 in the implant body 148 during rotation of the implant body by the tool 150. Such overtorquing could lead to difficulty in removing the tool 150 from the implant body 148 if the threaded areas 154 and 156 are engaged too strongly.

The invention has been described with reference to preferred embodiments. Obviously, modifications and alterations will occur to others upon the reading and understanding of the preceding specification. It is intended that the invention be construed as including all such alterations and modifications insofar as they come within the scope of the appended claims or the equivalents thereof.

I claim:

1. A prosthetic device adapted for fusing together adjoining vertebrae connected by tissue of a collapsed disc, comprising:

an inert generally rectangularly shaped support body configured to be seated on hard end plates of the vertebrae, said support body having solid top and bottom faces;

a first aperture located in one of said support body top and bottom faces; and, a first anchoring peg movably mounted in said first aperture, said first anchoring peg projecting away from said one of said top and bottom faces and adapted to extend into an associated first vertebra to secure said support body in place relative to the associated first vertebra wherein said first anchoring peg comprises a body having a tapered proximal end and an apertured distal end.

2. The device of claim 1 further comprising a second anchoring peg movably mounted in a second aperture located in another of said top and bottom faces of said support body, said second aperture being spaced from said first aperture, said second peg projecting away from said another of said top and bottom faces and adapted to extend into an associated second vertebra to secure said support body in place relative to the associated second vertebra.

3. The device of claim 1 wherein said first anchoring peg apertured distal end includes a serrated cutting face for digging into the associated first vertebra and a valley circumscribed by said cutting face for receiving bone from the associated first vertebra.

4. The device of claim 1 further comprising a means for preventing a rotation of said first peg in said support body.

5. The device of claim 1 wherein said support body comprises a three dimensional member having radiused corners which allow a rotation of the support body along its longitudinal axis.

6. The assembly of claim 5 wherein said support body is adapted to be inserted between the adjoining vertebrae in a first orientation in which said top and bottom faces do not contact the adjoining vertebrae, and said support body is adapted to be rotated along its longitudinal axis to a second orientation in which said top and bottom faces contact the adjoining vertebrae.

7. The device of claim 1 further comprising a means for locking said first peg in place in relation to said support body when said first peg has been projected outwardly of said support body.

8. The device of claim 1 wherein said support body comprises a hollow three dimensional member including six interconnected walls defining an interior cavity and at least one opening in each wall of said member to allow for ingrowth of osseous tissue into said interior cavity of said body.

9. A prosthetic device for supporting vertebrae in a vertebral column, comprising:

an inert generally rectangularly shaped support body configured to be seated on hard end plates of the vertebrae, said support body having solid top and bottom faces;

a central passageway located in said support body;

a pair of guide holes located in said support body, said guide holes extending substantially perpendicularly to said central passageway in opposite directions through a respective one of said top and bottom faces of said support body;

first and second retaining pegs movably mounted in a respective one of said guide holes, each peg extending away from said one of said top and bottom faces and adapted to extend into an associated vertebra to secure said support body in place relative to the associated vertebrae, each peg comprising a body having a distal end including a cutting edge and an adjacent aperture.

10. The device of claim 9 wherein said peg body of each of said retaining pegs further comprises a solid proximal end wall which is tapered for cooperating with a piston of an associated inserting tool.

11. The device of claim 9 wherein said retaining pegs each further comprise a means for preventing a rotation of said retaining peg in said support body.

12. The device of claim 9 wherein said support body further comprises at least one passage communicating with said central passageway and with an exterior surface of said support body for facilitating an ingrowth of a bone implant material and bone from the vertebrae to fuse the vertebrae together.

13. The device of claim 9 further comprising a means for locking said retaining pegs in place in relation to said support body when said retaining pegs have been projected outwardly of said support body.

14. The device of claim 9 wherein said support comprises a three-dimensional member having radiused corners which allow a rotation of said support body along its longitudinal axis.

15. A prosthetic device for supporting vertebrae in a spinal column, comprising:

an inert support body seatable within a cavity formed by removal of a portion of a disc located between adjoining vertebrae in a spinal column, said support body having top and bottom faces;

a first aperture located in one of said support body top and bottom faces; and, a first anchoring peg movably mounted in said first aperture, said first anchoring peg comprising an approximately cylindrical body having a tapered planar face on a proximal end thereof and a distal end including a centrally disposed conically-shaped aperture.

16. The device of claim 15 wherein said anchoring peg distal end further comprises an annular cutting face for digging into an associated vertebra.

17. The device of claim 16 wherein said annular cutting face is serrated.

18. A prosthetic assembly for fusing together adjoining vertebrae connected by tissue of a collapsed disc, comprising:

a pair of spaced support bodies, each being sized to be located on a respective side of a centerline of a vertebral column of a patient, each said support body including top and bottom faces;

a first aperture located in one of said support body top and bottom faces of at least one of said pair of support bodies; and, a first anchoring peg movably mounted in said first aperture, said first anchoring peg projecting away from said one of said top and bottom faces and adapted to extend into an associated first vertebra to secure said at least one of said pair of support bodies in place relative to the associated first vertebra, wherein said anchoring peg comprises:

a peg body having a serrated cutting edge for digging into the associated first vertebra, and an opening located adjacent said cutting edge for receiving bone from the associated vertebra.

19. The assembly of claim 18 wherein said serrated cutting edge is located on a distal end of said anchoring peg.

20. The assembly of claim 19 wherein a proximal end of said anchoring peg comprises a tapered planar face for cooperation with a piston of an associated inserting tool.

21. The assembly of claim 18 wherein said anchoring peg further comprises a means for preventing a rotation of said anchoring peg in relation to said at least one of said pair of support bodies.

22. The assembly of claim 18 wherein said at least one of said pair of support bodies further comprises:

a central passageway; and at least one passage communicating with said central passageway and with an exterior surface of said support body for facilitating an ingrowth of a bone implant material and bone from the associated vertebra to fuse the adjoining associated vertebrae together.

23. The assembly of claim 18 further comprising a means for locking said anchoring peg in place in relation to said at least one of said pair of support bodies when said anchoring peg has been projected outwardly of said at least one of said pair of support bodies.

24. The assembly of claim 18 wherein each of said support bodies comprises a three dimensional member having radiused corners which allow a rotation of each of said support bodies along their respective longitudinal axes from a first orientation, in which said support bodies are inserted between the adjoining vertebrae, to a second orientation in which said support bodies are installed between the adjoining vertebrae such that said top and bottom faces contact the adjoining vertebrae.

* * * * *